United States Patent [19]

Gabel et al.

[11] Patent Number: 5,095,164

[45] Date of Patent: Mar. 10, 1992

[54] PROCESS FOR CLEAVING ALKYL TERT.-ALKYL ETHERS

[75] Inventors: Christian Gabel; Bernhard Schleppinghoff; Hans-Dieter Köhler; Hans-Volker Scheef, all of Dormagen, Fed. Rep. of Germany

[73] Assignee: Ec Erdolchemie GmbH, Cologne, Fed. Rep. of Germany

[21] Appl. No.: 666,545

[22] Filed: Mar. 7, 1991

Related U.S. Application Data

[63] Continuation of Ser. No. 556,771, Jul. 23, 1990, which is a continuation of Ser. No. 482,596, Feb. 21, 1990, abandoned, which is a continuation of Ser. No. 221,822, Jul. 20, 1988, abandoned.

[30] Foreign Application Priority Data

Aug. 4, 1987 [DE] Fed. Rep. of Germany ....... 3725850
May 11, 1988 [DE] Fed. Rep. of Germany ....... 3816121

[51] Int. Cl.$^5$ .................................................. C07C 1/00
[52] U.S. Cl. ...................................... 585/640; 585/639; 568/866
[58] Field of Search .................. 585/639, 640; 568/866

[56] References Cited

U.S. PATENT DOCUMENTS

| 4,320,232 | 3/1982 | Volkamer et al. | 585/639 |
| 4,447,668 | 5/1984 | Smith, Jr. et al. | 585/639 |
| 4,536,605 | 8/1985 | Kida et al. | 585/640 |
| 4,751,343 | 6/1988 | Reinhard et al. | 585/639 |

FOREIGN PATENT DOCUMENTS

| 0008860 | 3/1980 | European Pat. Off. . |
| 0038129 | 10/1981 | European Pat. Off. . |
| 3210435 | 10/1982 | Fed. Rep. of Germany . |
| 3509292 | 12/1985 | Fed. Rep. of Germany . |
| 2096604 | 10/1982 | United Kingdom . |
| 2188333 | 9/1987 | United Kingdom . |

Primary Examiner—Curtis R. Davis
Assistant Examiner—E. D. Irzinski
Attorney, Agent, or Firm—Sprung Horn Kramer & Woods

[57] ABSTRACT

Alkyl tert.-alkyl ethers can be cleaved into the underlying alkanols and tert.-olefins in the presence of strongly acidic substances in a column apparatus, the strongly acidic substance being made available at the foot of the column. A particularly advantageous process design results when a water stream is fed below the top column tray in countercurrent to the tert.-olefin flowing upwards and is taken off again from the column above the bottom circulation; in the case of using an insoluble, strongly acidic substance, the latter is located in a catalyst bed at the foot of the column, and the alkyl tert.-alkyl ether is preferably fed in between the catalyst bed and the bottom circulation evaporator.

11 Claims, 1 Drawing Sheet

PROCESS FOR CLEAVING ALKYL TERT.-ALKYL ETHERS

This application is a continuation of application Ser. No. 556,771, filed July 23, 1990, now pending, which is a continuation of Ser. No. 482,596 filed Feb. 21, 1990, now abandoned, which is a continuation of Ser. No. 221,822, filed July 20, 1988, abandoned.

BACKGROUND OF THE INVENTION

The present invention relates to a process for cleaving alkyl tert.-alkyl ethers into the underlying alkanols and tert.-olefins in a column apparatus.

It is already known (DE-OS (German Published Specification) 3,210,435) to cleave methyl tert.-butyl ether (MTBE) in a column apparatus into methanol and i-butene, a cation exchanger based on sulphonated styrene/divinylbenzene resins being arranged as a catalyst in various column sections, between each of which column sections with 6 distillation trays but without cation exchanger are located. The MTBE is fed above the top catalyst bed. The flow of the liquid MTBE fed in and of the methanol produced during the reaction is downwards through the catalyst bed, and the gaseous i-butene formed, if appropriate as an azeotrope with methanol, flows upwards through the catalyst bed. With respect to the reaction conditions, the above DE-OS (German Published Specification) gives an indication of 5 bar and a column temperature between 45° C. (top temperature) and 100° C. (bottom temperature). In such a process, it is to be expected that 1. the column will easily flood due to the dense catalyst packing and hence severely lose separation effect and 2. the catalyst bed is continuously turned over by the liquid and gaseous streams flowing through in opposite directions, channel formation in the catalyst beds being highly probable. As a result of such channel formation, the major part of the catalyst mass would not come into contact with the substances flowing through, and its utilization would thus be completely unsatisfactory. The assembly of such a column apparatus, the introduction of the catalyst into the envisaged column sections and, of course, any replacement of the catalyst are involved and hence expensive. i-Butene, which is first formed in the lower catalyst layers, must flow on its upward path through all the catalyst layers and beds located above; during this, undesired dimerization to give diisobutylene cannot be excluded, which reduces the i-butene yield and causes additional difficulties in working up the bottom product. Similarly, methanol produced by cleavage in the upper catalyst layers is subject to the risk or formation of dimethyl ether on the acidic catalyst resin on its path to the column bottom. The formation of undesired by-products is further promoted by the high temperature in the lower part of the column.

SUMMARY OF THE INVENTION

A process for cleaving alkyl tert.-alkyl ethers into the underlying alkanols and tert.-olefins in the presence of strongly acidic substances in a column apparatus has been found, which is characterized in that the strongly acidic substance is made available at the foot of the column.

BRIEF DESCRIPTION OF THE DRAWING

The invention may be carried out in a column (1) provided with distillation and or extraction devices and further provided in the bottom circulation with a bed of a polymeric, strongly acidic substance. The alkyl tert.-alkyl ether to be cleaved is fed via the line (10); the tert.-olefin produced is taken off al the column top via (11).

DETAILED DESCRIPTION OF THE INVENTION

Figure 1:
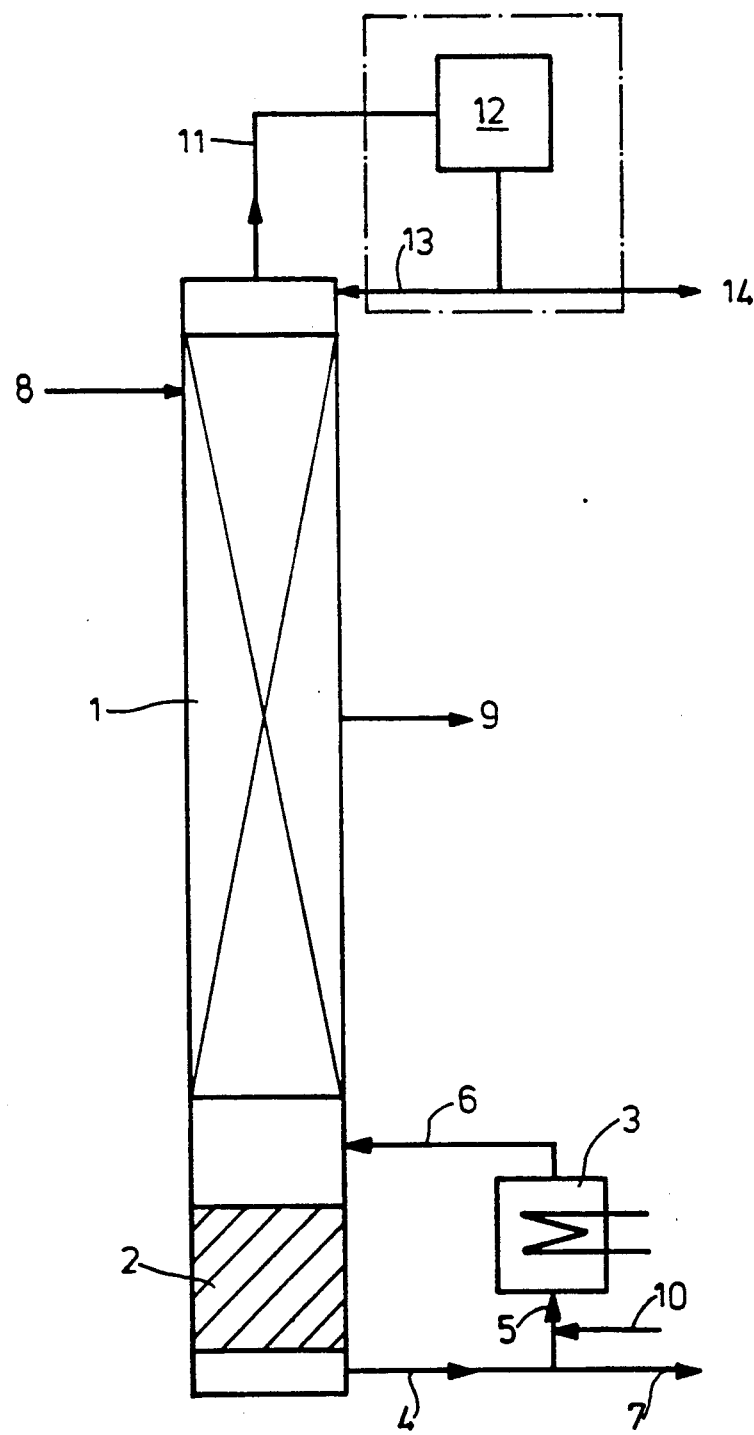

The primary or secondary $C_1$-$C_4$-alkanols such as methanol, ethanol, propanol, i-propanol, n-butanol or sec.-butanol may be mentioned as examples of underlying alkanols. The primary alkanols and, amongst these, methanol or ethanol in turn may be mentioned as being preferred; methanol is particularly preferred.

$C_4$-$C_7$-tert.-Olefins such as i-butene, i-amylenes, i-hexenes or i-heptenes may be mentioned as examples of underlying tert.-olefins. i-Butene and i-amylenes may be mentioned as being preferred.

The possible alkyl tert.-alkyl ethers are therefore: methyl tert.-butyl ether (MTBE), tert.-amyl methyl ether (TAME), methyl tert.-hexyl ether, methyl tert.-heptyl ether, ethyl tert.-butyl ether, ethyl tert.-amyl ether, ethyl tert.-hexyl ether, ethyl tert.-heptyl ether and others.

The strongly acidic substances which can be used are both soluble, low-molecular substances of inorganic or organic nature and insoluble, highly polymeric substances of inorganic or organic nature. The first group includes, for example, sulphuric acid, phosphoric acid, benzenesulphonic acid, toluenesulphonic acid, formic acid, trifluoromethanesulphonic acid and the like; within the range of their solubility, they effect the homogeneous catalytic cleavage of the said ethers. The second group includes substances such as acidic $SiO_2$, acidic $Al_2O_3$, polyphosphoric acids, certain fluorides, acidic zeolites such as mordenites and the like, and also neutral substances which have been treated with strong acids, such as silicas impregnated with $H_2SO_4$ or $H_3PO_4$, aluminas or other inorganic support materials, as well as sulphonated coals, and also organic, strongly acidic cation exchangers, all the substances mentioned being understood as the $H^+$ form; they effect a heterogeneous catalytic cleavage of the said ethers.

Amongst the said substances, the insoluble, highly polymeric substances are preferred, and particularly the strongly acidic cation exchangers in the $H^+$ form.

Examples of strongly acidic cation exchangers which can be used are those based on styrene/divinylbenzene resins, phenol/formaldehyde resins or coumarone/indene resins, the aromatic nuclei of which carry sulphonic acid groups. Preferably, the sulphonated styrene/divinylbenzene resins which are obtainable under various trade names can be used. These cation exchangers are used in the $H^+$ form.

The column apparatus used can be an apparatus such as is known to those skilled in the art for distillation and/or extraction purposes and is appropriately equipped.

According to the invention, the strongly acidic substance is made available at the foot of the column. Preferably, the strongly acidic substance is located in the bottom heater circulation of the column.

Soluble, low-molecular, strongly acidic substances can, for example, be fed into the lower part of the column, separately from or together with the ether which is to be cleaved. Theoretically, a single feed of the strongly acidic substance, which remains at the foot of the column, suffices, while the ether is decomposed into its cleaveage products and leaves the column in this form over the top thereof or at points above the bottom of the column; in practice, however, in order to remove undesired byproducts, a small purification stream is taken off at the foot of the column, and this always contains a little strongly acidic substance as a loss. Such losses are compensated by re-addition of the strongly acidic substance.

Insoluble polymeric substances of the said type do not show any losses via a purification stream and are therefore preferred. This applied to a particular extent to strongly acidic cation exchangers, which are therefore taken below as examples for the further description of the process according to the invention.

According to the invention, the bottom circulation thus always flows alternately through the cation exchanger as an example of an insoluble, polymeric, strongly acidic substance and through the indirect column heater which is operated electrically or by means of a separate heat carrier stream (steam, heat transfer fluid). The bottom circulation can here be effected by the convection caused by the bottom heater or as forced circulation by means of pumps. The forced circulation effected by a pump can here also be against the convection effect, so that it is possible in principle to recycle the bottom circulation into the column below its take-off point, so that the flow to the cation exchanger location in the bottom is from below. It is preferred, however, for the flow to the cation exchanger to be from above, and this can be effected by convection or by forced circulation.

In a surprisingly advantageous manner, the arrangement, according to the invention, of the cation exchanger as an example of an insoluble, polymeric, strongly acidic substance permits rapid removal of the cleavage products from the cation exchanger, so that secondary reactions of the tert.-olefin (to give the dimer) or of the alkanol (to give the dialkyl ether) can be effectively suppressed. Particularly in the case of the cleavage of methyl tert.-alkyl ethers, the formation of dimethyl ether, which makes the preparation of pure cleavage products very difficult, is suppressed. Furthermore, the immediate vicinity of the cation exchanger provided and the bottom heater makes it possible to set the temperature required for the cleavage of the alkyl tert.-alkyl ethers with very much greater accuracy and thus to avoid unnecessary thermal stresses on the reaction products.

The foot of the column, preferably the bottom circulation, is at a temperature of, for example, 50°-100° C., preferably 55°-85° C., particularly preferably 60°-80° C. In the case that alkyl tert.-alkyl ethers having more than 6 C atoms in total are cleaved, it may be necessary to raise the upper limit of the said temperature ranges by 10°-20° C. When the abovementioned inorganic, insoluble, strongly acidic substances are used, it can also be advantageous to employ temperatures of up to 200° C., preferably up to 160° C. In the case of the lower-boiling ethers amongst those mentioned above, the process can then be carried out, in the manner known to those skilled in the art, under such a pressure that a liquid phase is maintained at the foot of the column.

It is preferred to operate within the said temperature range, which may be the range of 50°-100° C. or, in the case of higher ethers, a range extended upwards by 10°-20° C. or, finally, the range extending up the 200° C., as described, at the maximum boiling point of the reaction mixture circulating in the bottom, which temperature is established as a result of the remaining column conditions. This ensures the most rapid degassing possible of the gaseous cleavage products flowing off upwards. Under the column conditions to be taken into account, special reference may be made to the pressure to be established. The process according to the invention can in principle also be carried out under a reduced pressure, but such a reduced pressure is less preferred because of the difficult condensation of the tert.-olefin at the column top, and it is used only in the case of tertiary olefins having more than 6 C atoms. The column is therefore preferably operated under normal or slightly elevated pressure, for example 1-5 bar. When operating under normal pressure, however, the column bottom is subject at least to the differential pressure known to those skilled in the art and depending on the column height.

The arrangement, according to the invention, of the cation exchanger allows flow velocities through the bottom circulation within a very wide range. These flow velocities are defined as LHSV (Liquid hourly space velocity) and assume values of $a = 1-100$, preferably 10-50, liters of bottom circulation per liter of cation exchanger per hour. The ether to be cleaved is added to the bottom circulation at a rate of 0.5-10, preferably 3-8, l of ether per l of cation exchanger per hour.

The tert.-olefin formed by the cleavage is taken off from the process according to the invention at the top of the column, if appropriate as an azeotrope with the alkanol produced at the same time. The major part of the alkanol produced by the cleavage is taken from the bottom outflow, together with small quantities of uncleaved ether and small quantities of by-products.

In an advantageous variant of the process according to the invention, a water stream is fed to the column below the upper column trays. This water stream effects washing of the tert.-olefin taken off at the column top and allows the alkanol produced in the cleavage to be taken off as a mixture with water from one of the lower trays above the column bottom. The feed of the alkyl tert.-alkyl ether to be cleaved is preferably below the take-off of the said water stream. The water rate here amounts to 2-6 parts by weight per 1 part by weight of the quantity of alkanol to be washed out.

In this advantageous process variant, only a small purification stream is taken from the bottom outflow, and this consists essentially of unconverted alkyl tert.-alkyl ether and small quantities of high boilers.

The process according to the invention in its advantageous variant described, using an insoluble, highly polymeric, strongly acidic substance, is explained by reference to the attached figure:

A column (1) provided with distillation and/or extraction devices was provided in the bottom circulation with a bed of insoluble, highly polymeric, strongly acidic substance (2). The bottom circulation also includes the indirect bottom heater (3), which shows in the figure, by way of example, that the flow of the bottom circulation is from above via the lines (4), (5) and (6) as a result of the convection flow (2) generated on (3). (7) is the take-off line for a purification stream (a little unconverted ether and higher boilers). Via (8), water is fed to the column and taken off again via (9); the water taken off via (9) contains at least a part of the alkanol produced the cleavage. The alkyl tert.-alkyl ether which is to be cleaved is fed via the line (10) to the column. The tert.-olefin produced in the cleavage is taken off at the column top via (11).

The tert.-olefin taken off via (11) is condensed in (12) and partially passed into the column as reflux via (13) and partially taken off as product via (14). For the case that the tert.-olefin is to be taken off as an azeotrope with alkanol via (11), especially if the washing water stream described above is omitted, the region containing (12) and (13), surrounded by a dashed line in the drawing, can be absent; (11) then leads directly into (14).

EXAMPLES

General Description of Experiments

The experiments were carried out in a pressure column of steel, having an internal diameter of 50 mm. Three column sections of one meter each were mounted on top of the evaporator. The column had 20 actual trays and was designed for an operating pressure of up to 20 bar. The structure corresponded to the attached drawing.

All the product streams leading into and out of the column were flow-controlled.

| Inputs | | |
|---|---|---|
| Ether | Feed | at the bottom of the column via (10) |
| Water | Feed | at the 18th tray of the column via (8) |
| Outputs | | |
| i-Amylene | Take-off | at the top of the column via (11) |
| i-Butene | Take-off | at the top of the column via (11) |
| Methanol | Take-off | at the 10th tray of the column via (9) |
| Methanol/water | Take-off | at the 10th tray of the column via (9) |

The evaporator was heated electrically.

A commercially available strongly acidic, macroporous styrene/divinylbenzene cation exchanger with $SO_3H$ groups (for example SPC 118 from Messrs. Bayer) was used as the catalyst for the ether cleavage in a bed in the circulating evaporator.

The ethers were used in a purity of >99%.

Deionized water was used as the washing water.

EXAMPLE 1

TAME Cleavage Alone in the Column

| Reaction conditions: | |
|---|---|
| Input TAME (by gas chromatography) | >99.9% by weight |
| Bottom temperature (= cleavage temperature) | 70.5° C. |
| Top temperature | 32.5° C. |
| Column pressure | 1.0 bar |
| Reflux ratio (reflux/take-off) | 4.0 |
| Catalyst quantity | 0.1 liter |
| Added TAME per hour | 0.6 liter |

| | | Materials: | | | |
|---|---|---|---|---|---|
| Input | | Output | | | |
| Item | Feed | Top | Side | Bottom | Total |
| Component: | | | | | |
| Total (g/h) | 438.0 | 247.9 | 167.1 | 23.0 | 438.0 |
| TAME (g/h) | 438.0 | <0.1 | 77.3 | 20.3 | 97.6 |
| i-Amylene (g/h) | <0.1 | 221.4 | 9.9 | 1.7 | 233.0 |
| Methanol (g/h) | <0.1 | 26.5 | 79.3 | 0.7 | 107.1 |
| Higher (g/h) | <0.1 | <0.1 | <0.1 | 0.3 | 0.3 |

TAME conversion 438.0 − 97.6 = 340.4 g (3.34 mol) = 77.7%
Yield of i-amylene: = 233.3 g (3.33 mol)
Yield of methanol: = 107.1 g (3.34 mol)

EXAMPLE 2

TAME Cleavage and Methanol Extraction in One Column

| Reaction conditions: | |
|---|---|
| Input TAME (by gas chromatography) | >99.9% by weight |
| Bottom temperature (= cleavage temperature) | 68.4° C. |
| Top temperature | 35.8° C. |
| Column pressure | 1.0 bar |
| Reflux ratio (reflux/take-off) | 4.0 |
| Catalyst quantity | 0.1 liter |
| LHSV (liquid hourly space velocity) | 6.0 |

| | | Materials: | | | |
|---|---|---|---|---|---|
| Input | | Output | | | |
| Item | Feed | Top | Side | Bottom | Total |
| Component: | | | | | |
| Total (g/h) | 1,038.0 | 284.0 | 731.0 | 23.0 | 1,038.0 |
| TAME (g/h) | 438.0 | <0.1 | <0.1 | 15.8 | 15.8 |
| Water (g/h) | 600.0 | <0.1 | 600.0 | 0.1 | 600.1 |
| i-Amylene (g/h) | <0.1 | 284.0 | <0.1 | 2.3 | 286.3 |
| Methanol (g/h) | <0.1 | <0.1 | 131.0 | 1.1 | 132.1 |
| Higher (g/h) | <0.1 | <0.1 | <0.1 | 3.7 | 3.7 |

TAME Conversion: 438.0 − 15.8 = 422.2 g (4.14 mol) = 96.3%
Yield of i-amylene: = 290.0 g (4.14 mol)
Yield of methanol: = 132.1 g (4.13 mol)

EXAMPLE 3

MTBE Cleavage and Methanol Extraction in One Column

| Reaction conditions: | |
|---|---|
| Input MTBE (by gas chromatography) | >99.9% by weight |
| Bottom temperature (= cleavage temperature) | 96.5° C. |
| Top temperature | 41.6° C. |
| Column pressure | 5.0 bar |
| Reflux ratio (reflux/take-off) | 6.5 |
| Catalyst quantity | 0.5 liter |
| LHSV (liquid hourly space velocity) | 8.0 |

| | | Materials: | | | |
|---|---|---|---|---|---|
| Input | | Output | | | |
| Item | Feed | Top | Side | Bottom | Total |
| Component: | | | | | |
| Total (g/h) | 6,960.0 | 1,700.0 | 4,970.0 | 290.0 | 6,960.0 |
| MTBE (g/h) | 2,960.0 | <0.1 | 46.0 | 237.0 | 283.0 |
| Water (g/h) | 4,000.0 | <0.1 | 4,000.0 | 0.1 | 4,000.0 |
| i-Butene (g/h) | <0.1 | 1,700.0 | <0.1 | 4.0 | 1,704.0 |

| | Materials: | | | |
|---|---|---|---|---|
| Input | | Output | | |
| Item | Feed | Top | Side | Bottom | Total |
| Methanol (g/h) | <0.1 | <0.1 | 924.0 | 49.0 | 973.0 |

MTBE conversion 2,960.0 − 290.0 = 2,670.0 g (30.4 mol) = 90.2%
Yield of i-butene = 1,704.0 g (30.4 mol)
Yield of methanol = 973.0 g (30.4 mol)

What is claimed is:

1. A process of cleaving alkyl tert.-alkyl ethers into the underlying alkanols and tert.-olefins comprising cleaving said ethers in the presence of strongly acidic substances in a column apparatus wherein the strongly acidic substance is present in the bottom heater circulation of the column of the column apparatus; the ether to be cleaved is introduced into the bottom heater circulation of the column; and a liquid phase is maintained in the bottom heater circulation of the column.

2. A process according to claim 1, wherein insoluble, highly polymeric, strongly acidic substances are used.

3. A process according to claim 2, wherein the strongly acidic substance are strongly acidic cation exchangers in the H+ form.

4. A process according to claim 2, wherein the LHSV (liquid hourly space velocity) at the insoluble, highly polymeric, strongly acidic substance is set to a=1–100 liters of bottom circulation per liter of insoluble, highly polymeric, strongly acidic substance per hour.

5. A process according to claim 4, wherein the LHSV is set to a=10 to 50.

6. A process according to claim 1, wherein the bottom circulation is at a temperature from 50° to 200° C.

7. A process according to claim 1, wherein the boiling point of the bottom circulation is that resulting from the column conditions.

8. A process according to claim 1, wherein the bottom circulation flowing to the strongly acidic cation exchanger in the H+ form is at a temperature from 50° to 100° C.

9. A process according to claim 8, wherein the bottom circulation flowing to the strongly acid cation exchanger in the H+ form is at a temperature from 55° to 80° C.

10. A process according to claim 9, wherein the bottom circulation flowing to the strongly acid cation exchanger in the H+ form is at a temperature from 60° to 80° C.

11. A process according to claim 1, wherein a water stream is fed below the upper column trays in countercurrent to the tert.-olefin, taken off as the top stream from the column, and is taken off again from the column above the column bottom, this water stream amounting to 2 to 6 parts by weight per 1 part by weight of the quantity of alkanol which is to be washed out.

* * * * *